United States Patent [19]

Hagan et al.

[11] Patent Number: 5,227,503
[45] Date of Patent: Jul. 13, 1993

[54] COSMETIC COMPOSITION

[75] Inventors: Desmond B. Hagan, South Wirral; Andrew Joiner, Liverpool; Richard J. Curtis, Wirral, all of Great Britain

[73] Assignee: Chesebrough Pond's USA Co., Division of Conopco, Inc., Greenwich, Conn.

[21] Appl. No.: 853,377

[22] Filed: Mar. 18, 1992

Related U.S. Application Data

[62] Division of Ser. No. 655,518, Feb. 13, 1991, Pat. No. 5,108,751.

[30] Foreign Application Priority Data

Feb. 13, 1990 [GB] United Kingdom ............... 03201

[51] Int. Cl.$^5$ ............................................. C07C 59/00
[52] U.S. Cl. ................................. 554/219; 554/213; 554/223; 554/224
[58] Field of Search ............... 554/213, 223, 230, 227, 554/219, 224

[56] References Cited

U.S. PATENT DOCUMENTS

| | | | |
|---|---|---|---|
| 4,393,043 | 7/1983 | Koulbanis et al. | 424/59 |
| 4,424,234 | 1/1984 | Alderson et al. | 424/317 |
| 4,510,093 | 4/1985 | Hulsmann | 260/410.9 |
| 4,950,688 | 8/1990 | Bowser et al. | 514/847 |

OTHER PUBLICATIONS

Chemical Abstracts, vol. 67, #3, p. 10182, 108156c, 1967.
Tetrahedron Letters, vol. 27, No. 37, pp. 4511-4514 (1986).
Tetrahedron Letters, vol. 23, No. 33, pp. 3419-3420 (1982).
Tetrahedron Letters, vol. 22, pp. 69-72 (1981).
J. Chem. Soc. Perk, Trans. I (1984) p. 331.
Roczniki Chemii, Ann Soc Chim. Polononum 36, 1791 (1962).

Primary Examiner—José G. Dees
Assistant Examiner—Deborah D. Com
Attorney, Agent, or Firm—Milton L. Honig

[57] ABSTRACT

The invention concerns 2-hydroxyalkenoic acids within a general formula

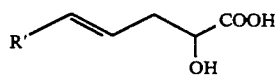

where R' is chosen from:
a. $C_wH_{2w}$,
b. $C_yH_{2y-1}$, and
c. $C_yH_{2y}OZ$
where Z is chosen from H, R" and $(CH_2)_nOR"$
R" is chosen from $C_mH_{2m+1}$ and $(CH_2)_nOC_mH_{2m+1}$;
w is an integer of from 1 to 25
y is an integer of from 2 to 25
m is an integer of from 1 to 4
n is an integer of from 1 to 6

Many compounds within the formula are novel and are claimed as such. The invention also provides a process for making the compounds, and compositions for topical application to human skin, hair or nails which contain compounds of the above formula and a cosmetically acceptable vehicle.

5 Claims, No Drawings

COSMETIC COMPOSITION

This is a divisional application of Ser. No. 07/655,518 filed Feb. 13, 1991, now U.S. Pat. No. 5,108,751.

FIELD OF INVENTION

The invention relates to unsaturated hydroxy acids, particularly 2-hydroxyalkenoic acids, to a process for preparing these acids, and to their use in compositions for topical application to skin, hair and nails.

BACKGROUND AND PRIOR ART i) Compounds per se

Very few 2-hydroxyalkenoic acids have been reported in the literature. These are:

2-hydroxy-4-hexenoic acid, whose synthesis is described in a paper by Mikami et al entitled "Novel silyl triflate-mediated [2,3] Wittig sigmatropic rearrangement. The possible interpretation of an oxygen ylide", published in Tetrahedron Lett. 1986, 27(37), 4511-14, and abstracted in Chem. Abs. (1987), 107, 77286h.

2-Hydroxy-4-heptenoic acid, whose synthesis is described in a paper by Achmatowicz et al entitled "Monoenic syntheses. I. On monoenophilic reactivity of ethyl mesoxalate", published in Roczniki Chem. 36 1791–1813 (1962), and abstracted in Chem. Abs. (1963), 59 8610d.

2-Hydroxy-4-octenoic acid, whose synthesis is described in a paper by Brenner et al, entitled "Some aspects of the chemistry of 1,1,1-trihaloalk-4-en-ols, the ene adducts obtained from reaction of chloral and bromal with alkenes", published in J. Chem. Soc., Perkin Trans. 1 1984 (3), 331–42, and abstracted in Chem. Abs. (1984), 101. 38095b.

2-Hydroxy-4-dodecenoic acid, whose synthesis is described in a paper by Takeshi et al entitled "Application of [2,3]sigmatropic rearrangements in organic synthesis. 111. The [2,3] Wittig rearrangement of 2-alkenyloxyacetic acids and its application to the stereocontrolled synthesis of β,γ-unsaturated aldehydes and conjugated dienoic acids", published in Tetrahedron Lett. 1981, 22(1), 69–72, and abstracted in Chem. Abs. (1981), 95, 6442d.

It is apparent that other 2-hydroxyalkenoic acids have not previously been disclosed in the literature, and an aspect of the invention is accordingly concerned with certain new 2-hydroxyalkenoic acids, and their synthesis.

ii) Cosmetic Compositions

A soft, supple and flexible skin has a marked cosmetic appeal and is an attribute of normal functioning epidermis. The outer layer of the epidermis, i.e. the stratum corneum, can, however, become dry and flaky following exposure to adverse climatic conditions, or excessive contact with detergents or solvents which result in loss of skin moisture, so that the skin loses its soft, supple and flexible characteristics. Emollients such as fats, phospholipids and sterols have in the past been used to soften dry skin, but it is apparent that these emollients are only partially effective as a remedy for this type of condition. Also, topical application to the skin of classical humectants is unlikely to alleviate this problem since they are not particularly skin substantive and are generally rinsed from the skin during washing.

It is therefore evident that there exists a need for an effective treatment for skin which is in a dry, flaky condition and which is relatively inflexible.

It has been proposed in U.S. Pat. No. 4,105,782 (Yu & Van Scott) to use amides or ammonium salts of α-hydroxyacids in the treatment of acne or dandruff and, in the Yu & Van Scott patents, U.S. Pat. No. 4,105,783 and U.S. Pat. No. 4,197,316, to use such compounds in the treatment of dry skin. U.S. Pat. No. 4,234,599 (Yu & Van Scott) discloses the use of α-hydroxyacids, and their esters or amine salts in the treatment of keratoses.

In U.S. Pat. No. 4,363,815 (Yu & Van Scott) it is proposed to use α-hydroxyacids or β-hydroxyacids or ketoacids or their derivatives, including inorganic salts, in a composition for treating skin conditions.

According to GB 1 471 679 (Avon), the use of alkali metal salts of $C_2$–$C_5$ α-hydroxycarboxylic acids in moisturising compositions is proposed.

In DE 2 110 993 (Henkel), there are disclosed alkali metal salts of $C_4$–$C_{10}$ α-hydroxycarboxylic acids, and the sodium salt of α-hydroxycaprylic acid is mentioned. These salts are incorporated in amounts from 3–30% into washing and cleaning compositions and are said to confer improved storage stability.

As part of a programme to examine substances for their ability to improve skin condition, isolated guinea pig footpad stratum corneum was selected as a model for human skin, and changes in its elasticity were measured after application of each test substance. The amount by which extensibility of the stratum corneum was increased was taken as a measure of the likely skin benefit that the substance would have on human skin.

Of the many substances screened in this way, certain 2-hydroxyalkanoic acids, as described in EP-B-O 007 785 (Unilever), were identified for their skin benefits when included in compositions for topical application to the skin. Such benefits include both increased elasticity of the skin, particularly the stratum corneum, and improved appearance. However, difficulty can be experienced when formulating certain of these 2-hydroxyalkanoic acids in skin cosmetic formulations, due to their poor solubility in water.

DEFINITION OF THE INVENTION COMPOUND PER SE

The invention accordingly provides 2-hydroxyalkenoic acid having the structure (1):

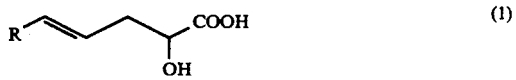

where R is chosen from:
a. $C_xH_{2x+1}$,
b. $C_yH_{2y-1}$, and
c. $C_yH_{2y}OZ$;

where Z is chosen from H, R" and $(CH_2)_nOR"$
R" is chosen from $C_mH_{2m+1}$ and $(CH_2)_nOC_mH_{2m+1}$;
x is an integer of from 4 to 6, or from 8 to 25
y is an integer of from 2 to 25
m is an integer of from 1 to 4
n is an integer of from 1 to 6.

In further aspects the invention also provides a process for preparing the unsaturated 2-hydroxyalkenoic acids, and skin, hair and nail treatment compositions incorporating unsaturated 2-hydroxyalkenoic acids.

DISCLOSURE OF THE INVENTION

The 2-hydroxyalkenoic acid

The unsaturated 2-hydroxyalkenoic acid has the structure (1):

$$R\diagup\!\!\!\diagdown\!\!\!\diagup\!\!\!\diagdown_{OH}^{COOH} \quad (1)$$

where R is chosen from:
a. $C_xH_{2x+1}$,
b. $C_yH_{2y-1}$, and
c. $C_yH_{2y}OZ$;
  where Z is chosen from H, R″ and $(CH_2)_nOR″$
    R″ is chosen from $C_mH_{2m+1}$ and $(CH_2)_nOC_mH_{2m+1}$;
  x is an integer of from 4 to 6, or from 8 to 25
  y is an integer of from 2 to 25
  m is an integer of from 1 to 4
  n is an integer of from 1 to 6.

The new 2-hydroxyalkenoic acids in accordance with the generic definition given herein are exemplified by three classes of new acids, namely:
mono-unsaturated 2-hydroxyalkenoic acids, di-unsaturated 2-hydroxyalkenoic acids, and mono-unsaturated oxa-2-hydroxyalkenoic acids (i.e. ether acids).

Examples of the new mono-unsaturated 2-hydroxyalkenoic acids, where R is $C_xH_{2x+1}$ include:
2-Hydroxy-4-nonenoic acid
2-Hydroxy-4-decenoic acid
2-Hydroxy-4-undecenoic acid
2-Hydroxy-4-tridecenoic acid
2-Hydroxy-4-tetradecenoic acid
2-Hydroxy-4-pentadecenoic acid
2-Hydroxy-4-hexadecenoic acid
2-Hydroxy-4-heptadecenoic acid
2-Hydroxy-4-octadecenoic acid
2-Hydroxy-4-nonadecenoic acid
2-Hydroxy-4-eicosenoic acid
2-Hydroxy-4-heneicosenoic acid
2-Hydroxy-4-docosenoic acid
2-Hydroxy-4-tricosenoic acid
2-Hydroxy-4-tetracosenoic acid
2-Hydroxy-4-pentacosenoic acid
2-Hydroxy-4-hexacosenoic acid
2-Hydroxy-4-heptacosenoic acid
2-Hydroxy-4-octacosenoic acid
2-Hydroxy-4-nonacosenoic acid, and
2-Hydroxy-4-triacontencoic acid.

Examples of the new di-unsaturated 2-hydroxyalkenoic acids, where R is $C_yH_{2y-1}$ include:
2-Hydroxy-4,7-octadienoic acid
2-Hydroxy-4,9-decadienoic acid
2-Hydroxy-4,10-undecadienoic acid
2-Hydroxy-4,11-dodecadienoic acid
2-Hydroxy-4,13-tetradecadienoic acid
2-Hydroxy-4,15-hexadecadienoic acid
2-Hydroxy-4,17-octadecadienoic acid
2-Hydroxy-4,19-eicosadienoic acid
2-Hydroxy-4,21-docosadienoic acid
2-Hydroxy-4,23-tetracosadienoic acid
2-Hydroxy-4,25-hexacosadienoic acid
2-Hydroxy-4,27-octacosadienoic acid, and
2-Hydroxy-4,29-triacontadienoic acid.

Examples of new mono unsaturated oxa-2-hydroxyalkenoic acids where R is $C_yH_{2y}OZ$ (ether acids) include:
2-Hydroxy-6-oxa-4-heptenoic acid
2-Hydroxy-7-oxa-4-octenoic acid
2-Hydroxy-9-oxa-4-decenoic acid
2-Hydroxy-9-oxa-4-undecenoic acid
2-Hydroxy-11-oxa-4-dodecenoic acid
2-Hydroxy-13-oxa-4-tetradecenoic acid
2-Hydroxy-13-oxa-4-pentadecenoic acid
2-Hydroxy-14-oxa-4-pentadecenoic acid
2-Hydroxy-13-oxa-14-methyl-4-pentadecenoic acid
2-Hydroxy-11,14-dioxa-4-pentadecenoic acid
2-Hydroxy-13-oxa-4-hexadecenoic acid
2-Hydroxy-14-oxa-4-hexadecenoic acid
2-Hydroxy-15-oxa-4-hexadecenoic acid
2-Hydroxy-17-oxa-4-octadecenoic acid
2-Hydroxy-14,17-dioxa-4-octadecenoic acid
2-Hydroxy-18-oxa-4-eicosenoic acid
2-Hydroxy-18-oxa-19-methyl-4-eicosenoic acid
2-Hydroxy-19-oxa-4-docosenoic acid
2-Hydroxy-18,21-dioxa-4-tricosenoic acid
2-Hydroxy-22-oxa-4-tetracosenoic acid
2-Hydroxy-25-oxa-4-hexacosenoic acid
2-Hydroxy-24-oxa-4-heptacosenoic acid
2-Hydroxy-25-oxa-4-octacosenoic acid
2-Hydroxy-23,26-dioxa-4-octacosenoic acid, and
2-Hydroxy-29-oxa-4-triacontenoic acid.

It is to be understood that the above examples of 2-hydroxyalkenoic acids are merely illustrative of the many acids covered by the generic structure (1) given herein before.

PROCESS FOR PREPARING THE 2-HYDROXYALKENOIC ACID

The process for preparing the 2-hydroxyalkenoic acids, as herein defined, is based on that described by Klimova et al, in a paper entitled "Catalytic monoene synthesis with carbonyl compounds. Addition of 1-alkenes to glyoxylic acid esters", published in Dokl. Akad. Nauk SSSR 173 (6), 1332–5 (1967) and abstracted in Chem Abs 67 (1967), 108156c.

The process according to the invention therefore comprises, in broad general terms, the steps of catalysing the reaction of an alkene and an alkyl glyoxalate to form, as an intermediate, a 2-hydroxyalkenoate ester, and subsequently hydrolysing this ester with a base in order to form the corresponding free 2-hydroxyalkenoic acid.

A preferred process for preparing the 2-hydroxy alkenoic acids according to the invention involves the use of methyl glyoxalate, as the alkyl glyoxalate, and stannic chloride as the catalyst, the alkene having the structure (2)

$$R\diagup\!\!\!\diagdown\!\!\!\diagup \quad (2)$$

the options for the group R being as herein defined for R in structure (1)

This aspect of the invention can accordingly be defined as a process for preparing a 2-hydroxyalkenoic acid, as defined herein, and having the structure (1), which process comprises the steps of:
  i) catalysing the reaction of an alkene having the structure (2):

(2)

with an alkyl glyoxalate having the structure (3)

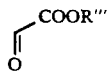
(3)

where R''' is $C_mH_{2m+1}$ and m is an integer of from 1 to 4;

to form an unsaturated hydroxy ester having the structure (4)

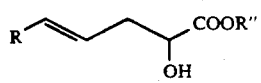
(4)

and ii) hydrolysing the unsaturated hydroxy ester to yield the corresponding 2-hydroxy alkenoic acid having the structure (1)

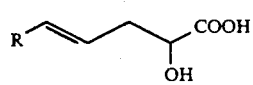
(1)

The steps of a preferred form of this process can be summarised as follows:

i. Dissolve methyl glyoxalate and the alkene in dichloromethane under nitrogen atmosphere and cool;
ii. Add stannic chloride, stir and allow to warm;
iii. Neutralise with triethylamine, add water and further dichloromethane;
iv. Separate organic layer, wash, dry, remove solvent and distill off ester product;
v. Hydrolyse ester with base under reflux conditions; and
vi. Wash solution with hexane, acidify solution and extract product, dry and then remove organic solvent to leave either liquid (purifiable by distillation) or solid (purifiable by crystallisation).

According to a preferred process, employing the above summary, the hydroxyalkenoic acids according to the invention can be prepared as follows:

Methyl glyoxalate (1.0 equivalents) and the requisite alkene (2.0 equivalents) are dissolved in dry dichloromethane under a nitrogen atmosphere. Stannic chloride (0.3 equivalents) is added dropwise with stirring and cooling (ice/water bath at approx 0° C.). After 30 minutes at this temperature, the reaction is allowed to warm to room temperature and stirred for a further 21 hours. The mixture is neutralised with triethylamine (0.3 equivalents), stirred for an additional 5 minutes before water and dichloromethane are added. The organic layer is separated, washed in turn with water and brine, dried over anhydrous magnesium sulphate and evaporated, with the crude product being purified by short path distillation to give the pure hydroxy ester.

This intermediate is treated with 20% w/v sodium hydroxide solution (water:methanol, 1:1) and heated under reflux for 1 hour. After the reaction mixture has cooled to room temperature, it is washed with hexane and the organic layer separated. The clear aqueous phase is acidified to pH 1 with concentrated hydrochloric acid, followed by extraction of product with diethylether. The organic layer is separated, washed with brine, dried over anhydrous magnesium sulphate and evaporated to dryness to yield the desired 2-hydroxy-4-alkenoic acid.

These aspects of the invention are further illustrated by the following Examples which describe synthesis of selected 2-hydroxy-4-alkenoic acids according to the invention and provide also characterising data of these new acids.

EXAMPLE 1

Synthesis of 2-Hydroxy-4-octadecenoic acid (5)

The synthesis of this acid is in accordance with the following scheme, in which hexadecene (6) is the alkene starting material.

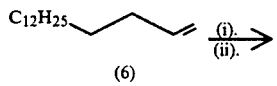
(6)

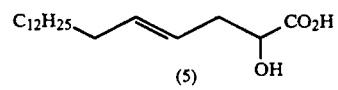
(5)

Reagents: (i). Methyl Glyoxalate, Stannic Chloride; (ii). NaOH hydrolysis i. Synthesis of the intermediate methyl 2-hydroxy-4-octadecenoate Methyl glyoxalate (8.80 g, 0.1 mol, 1.0 eq) and 1-hexadecene (44.80 g, 0.2 mol, 2.0 eq) are dissolved in dry dichloromethane (200 ml, freshly distilled from calcium hydride) under a nitrogen atmosphere. Stannic chloride (3.51 ml, 0.03 mol, 0.3 eq) is added dropwise with stirring and cooling at 0° C. (ice/water bath). After half an hour the reaction mixture is allowed to warm to room temperature and stirred for a further 21 hours before being neutralised with triethylamine (4.2 ml, 0.03 mol, 0.3 eq) with a further 5 minutes stirring. Water (50 ml) and dichloromethane (100 ml) are added, the organic layer is separated, washed in turn with water (50 ml) and brine (50 ml), dried over anhdyrous magnesium sulphate and evaporated. The crude oil is purified by short path distillation (bp 220–230° C./0.7 mm Hq) to furnish the ester product as a colourless liquid.

ii. Synthesis of 2-hydroxy-4-octadecenoic acid having the structure (5)

Methyl 2-hydroxy-4-octadecenoate (8.21 g, 0.026 mol, 1.0 eq) is heated under reflux with a large excess of sodium hydroxide (8.4 g, 0.21 mol, 8.1 eq) in water (20 ml) and methanol (20 ml) for 1 hour. After cooling down to room temperature, the mixture is washed with hexane (50 ml) and the organic phase separated. The clear aqueous layer is acidified to pH 1 with concentrated hydrochloric acid and the resultant mixture is extracted with diethylether (3×50 ml), the combined organic layers being washed with brine (50 ml) dried over anhydrous magnesium sulphate and evaporated to give a white solid. This is recrystallised from ethyl acetate/hexane to give the product acid (5) as white needles, 6.35 g (81%), mp 78–79.5° C.

Characterising spectral data were as follows: mp 78–79.5° C.; $\nu_{max}$ (nujol) 3440 and 1745 cm$^{-1}$; $\delta_H$ (360 MHz, d$_6$-DMSO) 0.90 (3H, t, 18-H$_3$, CH$_3$), 1.30 (22H, br s, 7 to 17-H$_2$, CH$_2$), 2.05 (2H, m, 6-H$_2$, CH$_2$CH=), 2.25–2.40 (2H, 2xm, 3-H$_2$, CH$_2$CHOH), 4.00 (1H, t, 2-H, CHOH) and 5.50 p.p.m. (2H, m, 4 and 5-H, CH=); C.I., M+298.

EXAMPLE 2

Synthesis of 2-hydroxy-4,9-decadienoic acid (7)

The synthesis of this acid is in accordance with the following scheme, in which 1,7-octadiene (8) is the alkene starting material.

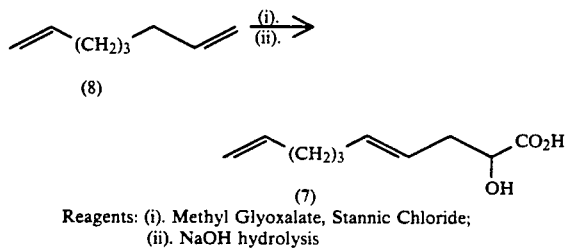

Reagents: (i). Methyl Glyoxalate, Stannic Chloride;
(ii). NaOH hydrolysis

The procedure for the synthesis of methyl 2-hydroxy-4,9-decadienoate, and its conversion to 2-hydroxy-4,9-decadienoic acid were essentially as described in Example 1, except that 1,7-octadiene was used as the alkene in place of hexadecene.

2-Hydroxy-4,9-decadienoic acid had a boiling point of 240-250° C. at 0.6 mm Hg, and possessed the following characterising spectral data: $\nu_{max}$ (liq film) 3500-2400 (br), 2950, 2920, 1725 (br), 1640, 1440, 1380, 1210, 1100, 990, 970 and 720 cm$^{-1}$; $\delta_H$ (360 MHz, CDCl$_3$) 1.45 (2H, m, 7-H$_2$, CH$_2$), 2.05 (4H, m, 6 and 8-H$_2$, CH$_2$CH=), 2.40 (1H, m, 3-H, CHCHOH), 2.60 (1H, m, 3-H, CHCHOH), 4.30 (1H, t, J=3.3 Hz, 2-H, CHOH), 5.00 (2H, m, 8-H$_2$, CH$_2$=), 5.40 (1H, m, 5-H, CH=), 5.65 (1H, m, 4-H, CH=) and 5.85 p.p.m. (1H, m, 7-H, CH=), C.I.; M+184.

EXAMPLE 3

Synthesis of 2-hydroxy-13-oxa-4-tetradecenoic acid (9)

The synthesis of this acid is in accordance with the following scheme, in which 11-oxa-1-dodecene (10) is the alkene starting material.

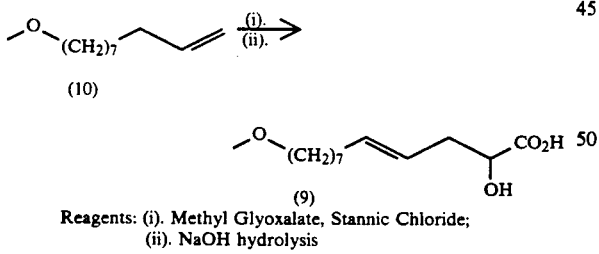

Reagents: (i). Methyl Glyoxalate, Stannic Chloride;
(ii). NaOH hydrolysis

The procedure for the synthesis of methyl 2-hydroxy-13-oxa-4-tetradecenoate and its conversion to 2-hydroxy-13-oxa-4-tetradecenoic acid were essentially as described in Example 1, except that 11-oxa-1-dodecene was used as the alkene in place of hexadecene.

2-Hydroxy-13-oxa-4-tetradecenoic acid had a melting point of 5-10° C., and possessed the following characterising spectral data: $\nu_{max}$ (liq film) 3400, 2930, 2860, 1720, 1250, 1100 and 970 cm$^{-1}$; $\delta H$ (360 MHz, CDCl$_3$) 1.25 (8H, br m, 7 to 10-H$_2$, CH$_2$), 1.55 (2H, m, 11-H$_2$, CH$_2$CH$_2$O), 2.00 (2H, m, 6-H, CH$_2$CH=), 2.40-2.60 (2H, 2×m, 3-H$_2$, CH$_2$CHOH), 3.35 (3H, s, 14-H$_3$, CH$_3$O), 3.40 (2H, t, 2-H$_2$, CH$_2$O), 4.30 (1H, t, 2-H, CHOH) and 5.40-5.65 (2H, 2×m, 4 and 5-H, CH=); C.I., M+2.44.

As mentioned, the invention also relates to a composition for topical application to human skin which comprises 2-hydroxy alkenoic acids, including both new acids as herein defined and other acids already reported in scientific literature, but whose utility is far removed from use in topical products.

As mentioned above, difficulty can be experienced when formulating certain 2-hydroxyalkenoic acids in skin cosmetic formulations, due to their poor solubility in water.

It has now surprisingly been discovered that certain 2-hydroxyalkenoic acids are much more soluble in water and are considerably easier to formulate than their corresponding saturated acids. Furthermore, topical application of these unsaturated acids to skin results in a substantial increase in skin flexibility, so that the pliability of the skin is improved.

The invention also concerns compositions containing the new 2-hydroxyalkenoic acids, as herein defined, which are suited to topical application to human skin, hair and nails. The invention is also concerned with compositions of a similar nature, and having a similar use, that comprise 2-hydroxyalkenoic acids whose identity have been disclosed in published literature, but whose reported utility is far removed from personal care products intended for topical application to human skin.

DEFINITION OF THE COMPOSITION OF THE INVENTION

The invention also provides a composition for topical application to human skin, hair or nails which comprises:

i. from 0.1 to 99.9% by weight of a 2-hydroxyalkenoic acid having the structure (20)

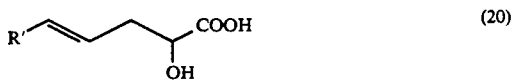

where R' is chosen from:
a. $C_wH_{2w}$,
b. $C_yH_{2y-1}$, and
c. $C_yH_{2y}OZ$
where Z is chosen from H, R" and (CH$_2$)$_n$OR"
R" is chosen from $C_mH_{2m+1}$ and (CH$_2$)$_n$OC$_m$H$_{2m+1}$;
w is an integer of from 1 to 25
y is an integer of from 2 to 25
m is an integer of from 1 to 4
n is an integer of from 1 to 6; and ii. from 0.1 to 99.9% by weight of a cosmetically acceptable vehicle for the acid.

The 2-hydroxyalkenoic acid

The composition according to the invention comprises a 2-hydroxyalkenoic acid or a mixture thereof, having the structure (20) as herein defined.

Examples of these 2-hydroxyalkenoic acids include:
2-hydroxy-4-hexenoic acid
2-hydroxy-4-heptenoic acid,
2-hydroxy-4-octenoic acid, and
2-hydroxy-4-dodecenoic acid.

Further examples of 2-hydroxyalkenoic acids, include the new mono-saturated acids, di-unsaturated acids and mono-unsaturated oxo-acids as herein defined.

The 2-hydroxyalkenoic acid is present in the composition according to the invention in an amount of from 0.1 to 90%, preferably from 0.5 to 10% and ideally from 1 to 5% by weight of the composition.

Synthesis of 2-hydroxyalkenoic acid

The 2-hydroxyalkenoic acids for use in the composition according to the invention can be prepared by the method described hereinbefore for the new 2-hydroxyalkenoic acids.

This aspect of the invention is illustrated by two more Examples which describe the synthesis and characterisation of two further 2-hydroxyalkenoic acids having the structure (20).

EXAMPLE 4

Synthesis of 2-Hydroxy-4-octenoic acid (21)

The synthesis of this acid is in accordance with the following scheme, in which 1-hexene (22) is the alkene starting material which is reacted with methyl glyoxalate to form methyl 2-hydroxy-4-octenoate (23) and then hydrolysed to form the free acid (21):

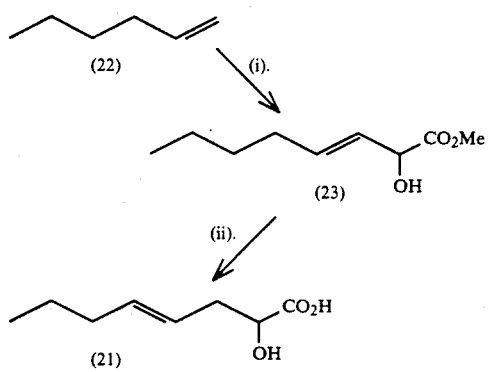

Reagents: (i). Methyl Glyoxalate, Stannic Chloride;
(ii). NaOH hydrolysis i. Synthesis of methyl ? -hydroxy-4-octenoate (23)

Methyl glyoxalate (8.80 g, 0.1 mol, 1.0 eq) and 1-hexene (16.80 g, 0.2 mol, 2.0 eq) are dissolved in dry dichloromethane (150 ml, freshly distilled from calcium hydride) under a nitrogen atmosphere. Stannic chloride (3.51 ml, 0.03 mol, 0.3 eq) is added dropwise with stirring and cooling at 0° C. (ice/water bath). After half an hour the reaction mixture is allowed to warm to room temperature and stirred for a further 21 hours before being neutralised with triethylamine (4.2 ml, 0.03 mol, 0.3 eq) with a further 5 minutes stirring. Water (50 ml) and dichloromethane (100 ml) are added, the organic layer is separated, washed in turn with water (50 ml) and brine (50 ml), dried over anhydrous magnesium sulphate and evaporated. The crude oil is purified by short path distillation (b p 120–130° C./0.7 mm Hg) to furnish the ester product (23) as a colourless liquid, 11.49 g (67% yield).

Characterization spectral data were as follows: $\nu$max (liq film) 3 500 (br), 2 960, 2 920, 1740, 1 440, 1 210 (br), 1 090 and 970 cm$^{-1}$; $\delta_H$ (360 MHz, CDCl$_3$) 0.9 (3H, t, J=8.0 Hz, 8-H$_3$, CH$_3$CH$_2$), 1.40 (2H, m, 7-H$_2$, CH$_2$CH$_3$), 2.00 (2H, m, 6-H$_2$, CH$_2$CH=), 2.40 (1H, m, 3-H, CHCHOH), 2.50 (1H, m, 3-H, CHCHOH), 2.75 (1H d, J=6.5 Hz, OH), 3.80 (3H,s, CH$_3$O), 4.25 (1H, m, 2-H, CHOH), 5.40 (1H, m, 5-H, CH=) and 5.60 p.p.m. (1H, m, 4-H, CH=); C.I., M+172.

ii. Synthesis of 2-hydroxy-4-octenoic acid (21)

Methyl 2-hydroxy-4-octenoate (23)(7.04 g, 0.041 mol, 1.0 eq) is heated under reflux with a large excess of sodium hydroxide (13.5 g, 0.34 mol, 8.3 eq) in water (30 ml) and methanol (30 ml) for 1 hour. After cooling down to room temperature, the mixture is washed with hexane (50 ml) and the organic phase separated. The clear aqueous layer is acidified to pH 1 with concentrated hydrochloric acid and the resultant mixture is extracted with diethylether (3×50 ml), the combined organic layers being washed with brine (50 ml) thence dried over anhydrous magnesium sulphate and evaporated to give a colourless oil which slowly crystallised to furnish the product acid (21) as a white waxy solid, 5.72 g (88%), m p 37–38° C.

Characterisation spectral data were as follows: $\nu$max (nujol) 3440, 2 820, 1695, 1420, 1150, 1095, 1045 and 920 cm$^{-1}$; $\delta_H$ (360 MHz, CDCl$_3$) 0.90 (3H, t, 8-H, CH$_3$), 1.40 (2H, m, 7-H$_2$, CH$_3$CH$_2$), 2.00 (2H, m, 6-H$_2$, CH$_2$CH=), 2.40-2.60(2H,m,3-H$_2$, CH$_2$CHOH), 4.30 (1H, t, CHOH), 5.40 (1H, m, 5-H, CH=) and 5.60 p.p.m. (1H, m, 4-H, CH=); C.I., M+158.

EXAMPLE 5

Synthesis of 2-Hydroxy-4-dodecenoic acid (24)

The synthesis of this acid is in accordance with the following scheme, in which 1-decene (25) is the alkene starting material.

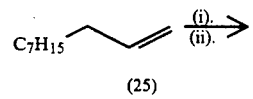

Reagents: (i). Methyl Glyoxalate, Stannic Chloride;
(ii). NaOH Hydrolysis

The procedure for the synthesis of methyl 2-hydroxy-4-dodecenoate, and its conversion to 2-hydroxy-4-dodecenoic acid were essentially as described in Example 4, except that 1-decene was used on the alkene in place of 1-hexene.

2-Hydroxy-4-dodecenoic acid had a melting point of 45–48° C. and possessed the following characterising spectral data:

$\nu$max (nujol) 3440, 3200–2500 (br), 1740, 1090, 965 and 720 cm$^{-1}$; $\delta_H$ (360 MHz, CDCl$_3$) 0.90 (3H, t, 12-H$_3$, CH$_3$), 1.20–1.40 (10 H, m, 7 to 11-H$_2$, CH$_2$), 2.00 (2H, m, 6-H$_2$, CH$_2$CH=), 2.45 (1H, m, 3-H, CHCHOH), 2.55 (1H, m, 3-H, CHCHOH), 4.30 (1H, t, 2-H, CHOH), 5.40 (1H, m, 5-H, CH=) and 5.60 p.p.m. (1H, m, 4-H, CH=); F.A.B., M+214.

The Cosmetically Acceptable Vehicle

The composition according to the invention also comprises a cosmetically acceptable vehicle, the selection of which will depend on the required product form of the composition. Typically, the vehicle will be chosen from diluents, dispersants or carriers for the 2-hydroxyalkenoic acid, so as to ensure an even distribution of it when applied to the skin.

Compositions according to this invention can include water as a vehicle, usually with at least one other cosmetically-acceptable vehicle.

Vehicles other than water that can be used in compositions according to the invention can include liquids or solids as emollients, solvents, humectants, thickeners and powders. Examples of each of these types of vehicles, which can be used singly or as mixtures of one or more vehicles, are as follows:

Emollients, such as stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polythylene glycol, triethylene glycol, lanolin, cocoa butter, corn oil, cotton seed oil, tallow, lard, olive oil, palm kernel oil, rapeseed oil, safflower seed oil, soybean oil, sunflower seed oil, olive oil, sesame seed oil, coconut oil, arachis oil, castor oil, acetylated lanolin alcohols, petroleum, mineral oil, butyl myristate, isostearic acid, palmitatic acid, isopropyl linoleate, lauryl lactate, myristyl lactate, decyl oleate, myristyl myristate;

Propellants, such as trichlorofluoromethane, dichlorodifluoromethane, dichlorotetrafluoroethane, monochlorodifluoromethane, trichlorotrifluoroethane, propane, butane, isobutane, dimethyl ether, carbon dioxide, nitrous oxide;

Solvents, such as ethyl alcohol, methylene chloride, isopropanol, acetone, castor oil, ethylene glycol monoethyl ether, diethylene glycol monobutyl ether, diethylene glycol monoethyl ether, dimethyl sulphoxide, dimethyl formamide, tetrahydrofuran;

Humectants, such as glycerin, sorbitol, sodium 2-pyrrolidone-5-carboxylate, soluble collagen, dibutyl phthalate, gelatin;

Powders, such as chalk, talc, fullers earth, kaolin, starch, gums, colloidal silicon dioxide, sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The cosmetically acceptable vehicle will usually form from 10 to 99.9%, preferably from 50 to 99% by weight of the composition, and can, in the absence of s other cosmetic adjuncts, form the balance of the composition.

Cosmetic Adjuncts

Examples of other conventional adjuncts, some of which can also function as vehicles, that may optionally be employed, include volatile and non-volatile silicones; silicone polymers; preservatives, such as para-hydroxy benzoate esters; humectants, such as butane-1,3-diol, glycerol, sorbitol, polyethylene glycol; stabilisers, such as sodium chloride or ammonium chloride; buffer system, such as lactic acid together with a base such as sodium hydroxide; oils and waxes, such as avocado oil, Evening Primrose oil, sunflower oil, beeswax, ozokerite wax, paraffin wax, lanolin, lanolin alcohol; emollients; thickeners; activity enhancers; colourants; whiteners; perfumes; emulsifiers; sunscreens; bactericides and water.

Cosmetic adjuncts can form up to 50% by weight of the composition and can conveniently form the balance of the composition.

Process for preparing the composition

The invention also provides a process for the preparation of a composition for topical application to human skin which comprises the step of incorporating the 2-hydroxyalkenoic acid, as herein defined, into the composition, together with a cosmetically acceptable vehicle.

Use of the composition

The composition according to the invention is intended primarily as a product for topical application to human skin, particularly dry skin, when repeated application can alleviate the dry condition, and restore the skin to a more natural, soft, supple, healthy state. The composition can also be used to treat the hair, including the scalp, and finger and toe nails.

In use, a small quantity of the composition, for example from 1 to 5 ml, is applied to the affected area of skin, hair or nails, from a suitable container or applicator and, if necessary, it is then spread over and/or rubbed into the skin, hair or nails using the hand or fingers or a suitable device.

PRODUCT FORMS AND PACKAGING

The topical skin treatment composition of the invention can be formulated as a fluid, for example in a product such as a lotion, with or without an applicator such as a roll-ball applicator, or a propellant-driven aerosol device or a container fitted with a pump to dispense the composition, for example as a mousse or simply for storage in a non-deformable bottle or squeeze container. Alternatively, the composition of the invention may be solid for example, as a bar or tablet, such as a soap bar, or semi-solid, for example as a cream, lotion, gel or ointment, for use in conjunction with a suitable applicator, or simply for storage in a tube or lidded jar.

The invention accordingly also provides a closed container containing a cosmetically acceptable composition as herein defined.

EVIDENCE OF THE SUPERIORITY OF THE INVENTION

The following experiments compare the extensibility of the stratum corneum when treated either with the 2-hydroxyalkenoic acid of the invention or with certain corresponding 2-hydroxyalkanoic acids.

Measurements of extensibility were made as described in EP-A 0 007 785. For each sample of stratum corneum, an extensibility ratio was calculated as the ratio of the extensibility measurement for a treated sample to the measurement for an untreated control sample.

Experiment 1

In accordance with this technique, an in vitro extensibility study was carried out on stratum corneum samples from guinea pig foot pads. Measurements of extensibility were made at a relative humidity of 62% and a temperature of 22° C. on batches of six samples of stratum corneum. These samples were treated with 0.06M aqueous solution of an acid maintained at pH 4.0 with sodium hydroxide.

The results are detailed in Table 1 below.

TABLE 1

All results are at 0.06 M concentration and at pH 4.0

| Acid | Extensibility Ratio | Relative Ratio |
|---|---|---|
| 2-Hydroxyoctanoic | 1.30 | 1.00 |
| 2-Hydroxypropionic (lactic) | 1.24 | 0.95 |
| 2-Hydroxydecanoic | 1.24 | 0.95 |
| 2-Hydroxydodecanoic | 1.28 | 0.98 |
| 2-Hydroxy-4-decenoic | 1.50 | 1.15 |
| 2-Hydroxy-4-dodecenoic | 1.46 | 1.12 |
| 2-Hydroxy-4,9-decadienoic | 1.72 | 1.32 |
| 2-Hydroxy-4,11-dodecadienoic | 1.52 | 1.17 |

The value for distilled water at pH 4.0 is approximately unity. It is evident that the use of the 2-hydroxyalkenoic acids leads to an increase in the ratio of up to 32% when compared to the use of the best 2-hydroxyalkanoic acid, i.e. 2-hydroxyoctanoic acid.

Experiment 2

This experiment compares the increase in extensibility conferred by aqueous solutions of acids at low pH. The tests were carried out on heat-separated guinea-pig footpads which were immersed in the required solution at the specified pH value. The extensibility ratios are shown in Table 2.

TABLE 2

| Acid | Concn. | pH | Extensibility Relative |
|---|---|---|---|
| 2-Hydroxypropionic | 0.20 M | 2.5 | 3.00 ± 0.65 |
| 2-Hydroxyoctanoic | 0.20 M | 2.5 | 5.90 ± 0.75 |
| 2-Hydroxy-13-oxa-4-tetradecenoic | 0.12 M | 2.9 | 12.35 ± 4.33 |

The extensibility ratio for the 2-hydroxy-13-oxa-4-tetradecenoic acid is significantly greater at the 99% confidence level than that of the 2-hydroxypropionic acid. The elasticity effect of this oxa acid is also significantly greater at the 98% confidence level than that of the 2-hydroxyoctanoic acid. Both the shorter acids were evaluated at a lower pH value and a higher concentration and still appear inferior to the oxa acid.

Experiment 3

This experiment compares the extensibility increase conferred in-vitro by solutions of several 2-hydroxyalkenoic acids against that conferred by 2-hydroxy octanoic acid. The tests were carried out on heat-separated guinea-pig footpads which were immersed in the required solution maintained at pH 4.0 by the addition of sodium hydroxide solution. The extensibility ratios for each group of samples are shown in Table 3.

TABLE 3 part i)
All the following results are at 0.06 M concentration.

| Acid | Extensiblity Ratio | Relative Ratio | Significance Level |
|---|---|---|---|
| 2-Hydroxy octanoic | 1.30 ± 0.27 | 1.00 | — |
| 2-Hydroxy-13-oxa-4-tetradecenoic | 2.53 ± 0.72 | 1.95 | 98% |
| 2-Hydroxy-13-oxa-4-pentadecenoic | 3.02 ± 0.82 | 2.23 | 99% |
| 2-Hydroxy-14-oxa-4-hexadecenoic | 2.46 ± 0.63 | 1.89 | 99% |
| 2-Hydroxy-14,17-dioxa-4-octadecenoic | 3.73 ± 1.78 | 2.87 | 95% |

TABLE 3

Part ii)
All the following results are at 0.12 M concentration.

| Acid | Extensiblity Ratio | Relative Ratio | Significance Level |
|---|---|---|---|
| 2-Hydroxy octanoic | 2.79 ± 0.71 | 1.00 | — |
| 2-Hydroxy-13-oxa-4-pentadecenoic | 4.49 ± 0.83 | 1.61 | 98% |
| 2-Hydroxy-14-oxa-4-pentadecenoic | 4.88 ± 1.22 | 1.75 | 98% |
| 2-Hydroxy-14-oxa 4-hexadecenoic | 4.44 ± 0.47 | 1.59 | 99% |
| 2-Hydroxy-14,17-dioxa-4-octadecenoic | 5.44 ± 1.47 | 1.95 | 98% |

Experiment 4

This experiment compares the elasticity effect conferred by an aqueous solution of an unsaturated acid with that conferred by an aqueous solution of the saturated equivalent acid. The evaluation was performed on heat-separated guinea-pig footpads which were immersed in the required solution maintained at pH 4.0. The results are shown in Table 4.

TABLE 4

All the following results are at 0.12 M concentration.

| Acid | Extensibility Ratio | Relative Ratio |
|---|---|---|
| 2-Hydroxy-4-oxa pentadecanoic | 1.76 ± 0.54 | — |
| 2-Hydroxy-14-oxa-4-pentadecenoic | 4.88 ± 1.22 | 2.77 |

The extensibility ratio for the 2-hydroxyalkenoic acid [2-hydroxy-14-oxa-4-pentadecenoic acid] is significantly greater at the 99% confidence level than that of the corresponding 2-hydroxyalkanoic acid 2-hydroxy-14-oxa-pentadecanoic acid].

EXAMPLES: COSMETIC COMPOSITIONS

The invention is further illustrated by the following examples.

Example 6

The example illustrates an oil-continuous (W/O) cream containing 2-hydroxy-4-tetradecenoic acid.

| Ingredients | % w/w |
|---|---|
| Silicone oils | 24.00 |
| Whitener | 0.15 |
| Humectants | 5.00 |
| 2-Hydroxy-4-tetradecenoic acid | 1.00 |
| Lactic acid | 5.00 |
| Potassium hydroxide | 4.00 |
| Water | 60.85 |
| | 100.00 |

The skin cream, having a pH value of 5, is made by the process, as herein described, by adding gradually to a mixture of silicones and whitener an aqueous mixture of the remaining ingredients and homogenising.

Example 7

This example illustrates an oil-continuous w/o cream containing 2-hydroxy-13-oxa-4-pentadecenoic acid, evening primrose oil and sunscreens.

| Ingredients | % w/w |
|---|---|
| Silicone oils | 25.00 |
| Whitener | 0.15 |
| Evening Primrose Oil | 3.00 |
| Humectants | 5.00 |
| Sunscreens | 4.00 |
| 2-Hydroxy-13-oxa-4-pentadecenoic acid | 1.50 |
| Sodium hydroxide | 2.00 |
| Sodium chloride | 2.00 |
| Lactic acid | 5.00 |
| Water | 52.35 |
| | 100.00 |

The skin cream, having a pH value of 4.5, is made by the process, as herein described, by adding gradually to a mixture of silicones and whitener an aqueous mixture of the remaining ingredients and homogenising.

Example 8

This example illustrates a oil-continuous (w/o) gel containing 2-hydroxy-4-dodecenoic acid.

| Ingredients | % w/w |
|---|---|
| Emulsifiers | 20.00 |
| Silicone oils | 20.00 |
| Humectant | 11.00 |
| 2-Hydroxy-4-dodecenoic acid | 1.00 |
| Sodium hydroxide | 4.55 |
| Lactic acid | 5.00 |
| Water | 38.45 |
| | 100.00 |

The gel, having a pH value of 5.5, is made by the process, as herein described, by adding to the silicone oils an aqueous mixture of the remaining ingredients and homogenising.

Example 9

This example illustrates a water-continuous (o/w) cream containing a 2-hydroxy-4-decenoic acid.

| Ingredients | % w/w |
|---|---|
| Thickener | 0.50 |
| Whitener | 0.15 |
| Humectant | 13.50 |
| Emulsifiers | 10.35 |
| Silicone oil | 7.60 |
| 2-Hydroxy-4-decenoic acid | 1.00 |
| Sodium Hydroxide | 5.00 |
| Lactic Acid | 3.00 |
| Water | 58.90 |
| | 100.00 |

The skin cream, having a pH value of 4, is made by the process, as herein described, by adding to a heated mixture of the thickener, humectant and 75% of the water. The remaining ingredients are added as an aqueous mixture with further homogenising.

Example 10

This example illustrates a water-continuous (o/w) cream containing 2-hydroxy-4,11-dodecadienoic acid, evening primrose oil and sunscreens.

| Ingredients | % w/w |
|---|---|
| Thickener | 0.50 |
| Whitener | 0.20 |
| Humectant | 10.00 |
| Evening Primrose Oil | 2.00 |
| Sunscreens | 3.00 |
| Emulsifiers | 10.50 |
| Silicone oil | 7.60 |
| 2-Hydroxy-4,11-dodecadienoic acid | 1.00 |
| Triethanolamine | 6.00 |
| Lactic acid | 4.00 |
| Water | 55.20 |
| | 100.00 |

The skin cream, having a pH value of 6, is made by the process, as herein described, by adding to a heated mixture of emulsifiers, silicone oil and whitener a mixture of the thickener, humectant and 75% of the water and homogenising. The remaining ingredients are added as an aqueous mixture with further homogenising.

Example 11

The example illustrates a night cream containing 2-hydroxy-4,21-docosadienoic acid and beeswax.

| Ingredients | % w/w |
|---|---|
| Silicone oil | 21.00 |
| Emulsifiers | 15.25 |
| Beeswax | 8.00 |
| Lanolin | 2.50 |
| 2-Hydroxy-4,21-docosadienic acid | 2.00 |
| Potassium hydroxide | 5.00 |
| Water | 46.25 |
| | 100.00 |

The night cream, having a pH value of 6.5, is made by the process, as herein described, by adding to a mixture of emulsifiers, silicone oil, beeswax and lanolin, a mixture of the remaining ingredients and homogenising.

Example 12

This example illustrates a lotion suitable for application to the hands containing 2-hydroxy-4-octenoic acid and lanolin.

| Ingredient | % |
|---|---|
| Emulsifiers | 10.00 |
| Lanolin | 2.50 |
| 2-Hydroxy-4-octenoic acid | 3.00 |
| Trethanolamine | 4.50 |
| Water | 80.00 |
| | 100.00 |

Example 13

This example illustrates a water-continuous (o/w) hand and body lotion containing 2-hydroxy-17-oxa-4-octadecenoic acid.

| Ingredient | % |
|---|---|
| Emulsifiers | 3.00 |
| Silicone oil | 5.00 |
| Thickener | 0.35 |
| Humectant | 9.45 |
| 2-Hydroxy-17-oxa-4-octadecenoic acid | 1.50 |
| Ammonium hydroxide | 3.95 |
| Ammonium chloride | 2.00 |
| Water | 74.75 |

-continued

| Ingredient | % |
|---|---|
| | 100.00 |

Example 14

This example illustrates a wash-off/wipe-off cleansing cream containing 2-hydroxy-4-hexenoic acid and chamomile.

| Ingredient | % |
|---|---|
| Mineral oil | 10.00 |
| Emulsifier | 3.00 |
| Chamomile distillate | 0.50 |
| 2-Hydroxide-4-hexenoic acid | 1.00 |
| Triethanolamine | 2.80 |
| Water | 82.70 |
| | 100.00 |

Example 15

This example illustrates a wash-off/wipe-off cleansing lotion containing 2-hydroxy-4,15-hexadecadienoic acid and beeswax.

| Ingredients | % w/w |
|---|---|
| Mineral oil | 45.00 |
| Emulsifier | 3.20 |
| Beeswax | 8.00 |
| Thickener | 10.00 |
| Perfume | 0.20 |
| 2-Hydroxy-4,15-hexadecadienoic acid | 1.00 |
| Triethanolamine | 4.00 |
| Water | 28.60 |
| | 100.00 |

The cleansing lotion, having a pH of 5.5, is made by the process, as herein described, by adding to a mixture of emulsifier, mineral oil and beeswax a mixture of the remaining ingredients and homogenising.

Example 16

The example illustrates a facial-washing foam containing 2-hydroxy-23,26-dioxa-4-octacosenoic acid and azulene.

| Ingredient | % w/w |
|---|---|
| Emulsifier | 20.00 |
| Thickener | 3.00 |
| Foam Booster | 25.00 |
| Humectant | 10.00 |
| Azulene crystals | 0.25 |
| Bentone | 0.50 |
| 2-Hydroxy-23,26-dioxa-4-octacosenoic acid | 2.50 |
| Potassium hydroxide | 4.50 |
| Water | 34.25 |
| | 100.00 |

Example 17

This example illustrates a conventional soap bar containing 2-hydroxy-4-docosenoic acid.

| Ingredient | % w/w |
|---|---|
| Anionic detergent | 18.00 |

-continued

| Ingredient | % w/w |
|---|---|
| Foam aid | 8.00 |
| Sodium hydroxide | 12.00 |
| Hardening agent | 2.00 |
| Alkaline silicate | 2.00 |
| Calcite | 12.00 |
| Talc | 10.00 |
| 2-Hydroxy-4-docosenoic acid | 2.00 |
| Water | 34.00 |
| | 100.00 |

Example 18

This example illustrates an all-purpose face-mask containing 2-hydroxy-4-hexacosenoic acid and phytoconcentrol camomile.

| Ingredient | % w/w |
|---|---|
| Kaolin | 30.00 |
| Mineral oil | 10.00 |
| Paraffin wax | 10.00 |
| Bentonite | 4.00 |
| 2-Hydroxy-4-hexacosenoic acid | 1.40 |
| Sodium hydroxide | 4.20 |
| Phytoconcentrol camomile | 0.25 |
| Water | 40.15 |
| | 100.00 |

The mask is made by the process, as herein described, by blending the mixture of the ingredients.

Example 19

This example illustrates a solution used to condition hair containing 2-hydroxy-4-hexadecenoic acid.

| Ingredient | % w/w |
|---|---|
| Emulsifier | 0.80 |
| 2-Hydroxy-4-hexadecenoic acid | 0.50 |
| Sodium chloride | 0.50 |
| Sodium hydroxide | 2.00 |
| Water | 96.20 |
| | 100.00 |

Example 20

The example illustrates a gel suitable for treating hair containing 2-hydroxy-19-methyl-18-oxa-4-eicosenoic acid and alpha-bisabolol.

| Ingredient | % w/w |
|---|---|
| Emulsifiers | 20.00 |
| Silicone oil | 20.00 |
| Humecant | 11.00 |
| Lactic acid | 5.00 |
| 2-Hydroxy-19-methyl-18-oxa-4-eicosenoic acid | 1.50 |
| Alpha-bisabolol | 0.20 |
| Triethanolamine | 4.55 |
| Fragrance | 0.10 |
| Water | 37.65 |
| | 100.00 |

Example 21

The example illustrates a nail strenthener suitable for treating dryness and brittleness, containing 2-hydroxy-4-tetracosenoic acid.

| Ingredient | % w/w |
|---|---|
| Humectant | 10.00 |
| Mineral oil | 10.00 |
| 2-Hydroxy-4-tetracosenoic acid | 2.00 |
| Potassium hydroxide | 4.50 |
| Water | 73.50 |
| | 100.00 |

Example 22

The example illustrates a lotion suitable for treatment of nails, containing 2-hydroxy-4,9-decadienoic acid and beeswax.

| Ingredient | % w/w |
|---|---|
| Propane-1,2-diol | 50.00 |
| Ethanol | 10.00 |
| Beeswax | 5.00 |
| 2-Hydroxy-4,9-decadienoic acid | 3.00 |
| Sodium chloride | 3.00 |
| Sodium hydroxide | 4.25 |
| Water | 24.75 |
| | 100.00 |

This lotion, having a pH value of 4.3, is made by the process, as herein described, by homogenising the mixture of the ingredients.

We claim:

1. A 2-hydroxyalkenoic acid having the structure (1):

$$R\diagup\!\!\!\diagdown\!\!\!\diagup\!\!\!\diagdown_{OH}^{COOH} \qquad (1)$$

where R is chosen from:
- a. $C_xH_{2x+1}$,
- b. $C_yH_{2y-1}$, and
- c. $C_yH_{2y}OZ$;

where Z is chosen from H, R" and $(CH_2)_nOR"$
R" is chosen from $C_mH_{2m+1}$ and $(CH_2)_nOC_mH_{2m+1}$;
x is an integer of from 4 to 6, or from 8 to 25
y is an integer of from 2 to 25
m is an integer of from 1 to 4
n is an integer of from 1 to 6.

2. A 2-hydroxyalkenoic acid according to claim 1, chosen from:

2-Hydroxy-4-nonenoic acid
2-Hydroxy-4-decenoic acid
2-Hydroxy-4-undecenoic acid
2-Hydroxy-4-tridecenoic acid
2-Hydroxy-4-tetradecenoic acid
2-Hydroxy-4-pentadecenoic acid
2-Hydroxy-4-hexadecenoic acid
2-Hydroxy-4-heptadecenoic acid
2-Hydroxy-4-octadecenoic acid
2-Hydroxy-4-nonadecenoic acid
2-Hydroxy-4-eicosenoic acid
2-Hydroxy-4-heneicosenoic acid
2-Hydroxy-4-docosenoic acid
2-Hydroxy-4-tricosenoic acid
2-Hydroxy-4-tetracosenoic acid
2-Hydroxy-4-pentacosenoic acid
2-Hydroxy-4-hexacosenoic acid
2-Hydroxy-4-heptacosenoic acid
2-Hydroxy-4-octacosenoic acid
2-Hydroxy-4-nonacosenoic acid, and
2-Hydroxy-4-triacontencoic acid.

3. A 2-hydroxyalkenoic acid according to claim 1, chosen from:

2-Hydroxy-4,7-octadienoic acid
2-Hydroxy-4,9-decadienoic acid
2-Hydroxy-4,10-undecadienoic acid
2-Hydroxy-4,11-dodecadienoic acid
2-Hydroxy-4,13-tetradecadienoic acid
2-Hydroxy-4,15-hexadecadienoic acid
2-Hydroxy-4,17-octadecadienoic acid
2-Hydroxy-4,19-eicosadienoic acid
2-Hydroxy-4,21-docosadienoic acid
2-Hydroxy-4,23-tetracosadienoic acid
2-Hydroxy-4,25-hexacosadienoic acid
2-Hydroxy-4,27-octacosadienoic acid, and
2-Hydroxy-4,29-triacontadienoic acid.

4. A 2-hydroxyalkenoic acid according to claim 1, chosen from:

2-Hydroxy-6-oxa-4-heptenoic acid
2-Hydroxy-7-oxa-4-octenoic acid
2-Hydroxy-9-oxa-4-decenoic acid
2-Hydroxy-9-oxa-4-undecenoic acid
2-Hydroxy-11-oxa-4-dodecenoic acid
2-Hydroxy-13-oxa-4-tetradecenoic acid
2-Hydroxy-13-oxa-4-pentadecenoic acid
2-Hydroxy-14-oxa-4-pentadecenoic acid
2-Hydroxy-13-oxa-14-methyl-4-pentadecenoic acid
2-Hydroxy-11,14-dioxa-4-pentadecenoic acid
2-Hydroxy-13-oxa-4-hexadecenoic acid
2-Hydroxy-14-oxa-4-hexadecenoic acid
2-Hydroxy-15-oxa-4-hexadecenoic acid
2-Hydroxy-17-oxa-4-octadecenoic acid
2-Hydroxy-14,17-dioxa-4-octadecenoic acid
2-Hydroxy-18-oxa-4-eicosenoic acid
2-Hydroxy-18-oxa-19-methyl-4-eicosenoic acid
2-Hydroxy-19-oxa-4-docosenoic acid
2-Hydroxy-18,21-dioxa-4-tricosenoic acid
2-Hydroxy-22-oxa-4-tetracosenoic acid
2-Hydroxy-25-oxa-4-hexacosenoic acid
2-Hydroxy-24-oxa-4-heptacosenoic acid
2-Hydroxy-25-oxa-4-octacosenoic acid
2-Hydroxy-23,26-dioxa-4-octacosenoic acid, and
2-Hydroxy-29-oxa-4-triacontenoic acid.

5. A process for preparing a 2-hydroxyalkenoic acid having the structure (1):

$$R\diagup\!\!\!\diagdown\!\!\!\diagup\!\!\!\diagdown_{OH}^{COOH} \qquad (1)$$

where R is chosen from:
- a. $C_xH_{2x+1}$,
- b. $C_yH_{2y-1}$, , and
- c. $C_yH_{2y}OZ$;

where Z is chosen from H, R" and $(CH_2)_nOR"$
R" is chosen from $C_mH_{2m+1}$ and $(CH_2)_nOC_mH_{2m+1}$;
x is an integer of from 4 to 6, or from 8 to 25;
y is an integer of from 2 to 25;
m is an integer of from 1 to 4; and
n is an integer of from 1 to 6;

wherein the process comprises the steps of:
(i) catalyzing the reaction of an alkene having the structure (2):

 (2)
with an alkyl glyoxalate having the structure (3):
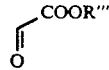 (3)
where R''' is $C_mH_{2m+1}$
and m has the value as herein defined; to form an unsaturated hydroxyester having the structure (4):
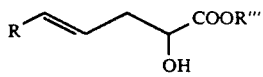 (4)
and
(ii) hydrolyzing the ester to yield the corresponding 2-hydroxyalkenoic acid.
* * * * *